US006635597B1

(12) United States Patent
Marks et al.

(10) Patent No.: US 6,635,597 B1
(45) Date of Patent: Oct. 21, 2003

(54) PERFLUORONAPHTHYL SUBSTITUTED BORON CONTAINING CATALYST ACTIVATOR

(75) Inventors: Tobin J. Marks, Evanston, IL (US); Liting Li, Evanston, IL (US); You-Xian Chen, Chicago, IL (US); Mark H. McAdon, Midland, MI (US); Peter N. Nickias, Midland, MI (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 09/463,713
(22) PCT Filed: Jul. 7, 1998
(86) PCT No.: PCT/US98/14052
§ 371 (c)(1),
(2), (4) Date: May 12, 2000
(87) PCT Pub. No.: WO99/06412
PCT Pub. Date: Feb. 11, 1999

Related U.S. Application Data

(60) Provisional application No. 60/054,587, filed on Aug. 1, 1997.

(51) Int. Cl.[7] ............................ B01J 21/02; C07F 5/02; C08F 4/52
(52) U.S. Cl. .................. 502/202; 502/150; 502/203; 526/134; 526/160; 556/7; 556/8; 556/9; 568/6
(58) Field of Search ................................ 502/150, 202, 502/203; 526/134; 556/7, 8, 9; 568/6

(56) References Cited

U.S. PATENT DOCUMENTS 5,541,349 A * 7/1996 Wilson et al. ................ 556/10
5,856,256 A * 1/1999 Marks et al. ............... 502/152

FOREIGN PATENT DOCUMENTS

WO    WO97/14698    * 4/1997
WO    WO 97 29845    8/1997

OTHER PUBLICATIONS

Chen et al. Organometallics 16 (1997) 3649–3657.*
Chen et al. J. Amer. Chem. Soc. 118 (1996) 12451–12452.*
Li, Liting et al., "The new organo–Lewis acid cocatalyst PNB for metallocene–mediated Ziegler–Natta alpha–olefin polymerizations", Book of Abstracts, 214th ACS National Meeting, Las Vegas, NV, Sep. 7–11. (1997).
Newton, Joanna et al., "Synthesis of polysilanes using group IV metallocene based catalysts and unusual boron based co–catalysts", Polym. Prepr. (Am. Chem. Soc. Div. Polym. Chem.) (1998), 39(1), 587–588.
Chen, You–Xian et al., "Organo–Lewis Acids as Cocatalysts in Cationic metallocene Polymerization Catalysts. Unusual Characteristics of Satirically Encumbered Tris (perfluorobiphenyl) borane" J. Am. Chem. Soc. (1996) 118(49), pp. 12451–12452.
Chen, You–Xian et al., "Constrained Geometry Dialkyl Catalysts. Efficient syntheses, C–H Bond Activation Chemistry Monomer–Dimer Equilibration and alpha–olefin Polymerization Catalysts", Organometallics (1997) 16(16) 3649–3657.

* cited by examiner

Primary Examiner—David W. Wu
Assistant Examiner—R. Rabago
(74) Attorney, Agent, or Firm—Welsh & Katz, Ltd.

(57) ABSTRACT

A catalyst activator particularly adapted for use in the activation of metal complexes of metals of Group 3–10 for polymerization of ethylenically unsaturated polymerizable monomers, especially olefins, comprising a neutral (Lewis acid) or charge separated (cation/anion pair) comprising a boron ligand containing a fluorinated organic group containing from 10 to 1000 non-hydrogen atoms.

2 Claims, No Drawings

PERFLUORONAPHTHYL SUBSTITUTED BORON CONTAINING CATALYST ACTIVATOR

This application claims the benefit of U.S. Provisional Application No. 60/054,587, filed Aug. 1, 1997.

This invention is made with government support under Federal Grant #DOE 86ER13511. The government has certain rights in the invention.

The present invention relates to a compound that is useful as a catalyst activator. More particularly the present invention relates to such compounds that are particularly adapted for use in the addition polymerization of unsaturated compounds in combination with a Group 3–10 metal complex, said activator comprising at least one perfluoronaphthyl substituted boron compound. Such an activator is particularly advantageous for use in a polymerization process wherein catalyst, catalyst activator, and at least one polymerizable monomer are combined under polymerization conditions to form a polymeric product.

It is previously known in the art to activate Ziegler-Natta polymerization catalysts, particularly such catalysts comprising Group 3–10 metal complexes containing delocalized π-bonded ligand groups, by the use of Bronsted acid salts capable of transferring a proton to form a cationic derivative of such Group 3–10 metal complex. Preferred Bronsted acid salts are such compounds containing a cation/anion pair that are capable of rendering the Group-3–10 metal complex catalytically active. Suitable activators comprise fluorinated arylborate anions, preferably tetrakis(pentafluoro-phenyl) borate anions. Additional suitable anions include sterically shielded diboron anions corresponding to the formula:

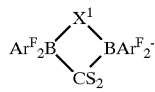

wherein:
S is hydrogen, alkyl, fluoroalkyl, aryl, or fluoroaryl; Ar$^F$ is fluoroaryl, and X$^1$ is either hydrogen or halide, disclosed in U.S. Pat. No. 5,447,895. Additional examples include carborane compounds such as are disclosed and claimed in U.S. Pat. No. 5,407,884.

Examples of preferred charge separated (cation/anion pair) activators are protonated ammonium, sulfonium, or phosphonium salts capable of transferring a hydrogen ion, disclosed in U.S. Pat. No. 5,198,401, U.S. Pat. No. 5,132,380, U.S. Pat. No. 5,470,927, and U.S. Pat. No. 5,153,157, as well as oxidizing salts such as carbonium, ferrocenium and silyilium salts, disclosed in U.S. Pat. No. 5,350,723, U.S. Pat. No. 5,189,192 and U.S. Pat. No. 5,626,087.

Further suitable activators for the above metal complexes include strong Lewis acids including tris(perfluorophenyl)borane and tris(perfluorobiphenyl)borane. The former composition has been previously disclosed for the above stated end use in EP-A-520,732, whereas the latter composition is similarly disclosed by Marks, et al., in *J. Am. Chem. Soc.*, 118, 12451–12452 (1996).

Despite the satisfactory performance of the foregoing catalyst activators under a variety of polymerization conditions, there is still a need for improved cocatalysts for use activation of various metal complexes under a variety of reaction conditions. Accordingly, it would be desirable if there were provided catalyst activators that could be employed in solution, slurry, gas phase or high pressure polymerizations and under homogeneous or heterogeneous process conditions having improved activation properties.

According to the present invention there is now provided Group 13 containing compounds in neutral (Lewis acid) or charge separated (cation/anion pair) form, corresponding to the formula:

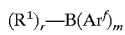

wherein:
B is boron;
R$^1$ independently each occurrence is a monovalent, anionic ligand group, with the proviso that for cationic compounds, one R$^1$ additionally comprises a dissociated cation moiety;
Ar$^f$ independently each occurrence is a monovalent, fluorinated organic group containing from 10 to 100 non-hydrogen atoms,
r is 0, 1, 2 or 3, and
m is 1, 2 or 3;
with the proviso that the sum of r and m is 3 or 4, and if r+m=3, then B is neutral and if r+m=4, then B is negatively charged, said charge being balanced by a cation component of one R$^1$.

Additionally according to the present invention there is provided a catalyst composition capable of polymerizing an ethylenically unsaturated, polymerizable monomer comprising, in combination, a Group 3–13 metal complex and the above described Group 13 compound, or the reaction product resulting from such combination.

Additionally according to the present invention there is provided a process for polymerization of one or more ethylenically unsaturated, polymerizable monomers comprising contacting the same, optionally in the presence of an inert aliphatic, alicyclic or aromatic hydrocarbon, with the above described catalyst composition.

The foregoing Group 13 compounds are uniquely capable of forming monomeric and dimeric cationic metal complexes from neutral metallocene complexes under certain operating conditions. They are also uniquely adapted for use in activation of a variety of metal complexes, especially Group 4 metal complexes, under standard and atypical polymerization conditions, and give improved yields of resulting olefin polymer.

All references herein to elements belonging to a certain Group refer to the Periodic Table of the Elements published and copyrighted by CRC Press, Inc., 1995. Also any reference to the Group or Groups shall be to the Group or Groups as reflected in this Periodic Table of the Elements using the IUPAC system for numbering groups. When, in reference to a cation portion of any compound herein, it is stated that a ligand group comprises such cation, it is to be understood that the cation is not chemically or physically incorporated in said ligand, or necessarily chemically attached thereto, in as much as the cation may freely dissociate from the anion portion of the compound. Rather, such ligand group is said to "comprise" the cation in order to properly account for the correct number of cations as dictated by considerations of charge balance.

The compounds of the invention are further characterized in the following manner. Preferred examples of suitable neutral Lewis acids according to the present invention correspond to the formula:

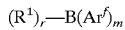

wherein:
R$^1$ independently each occurrence is a monovalent, anionic ligand group containing from 1 to 1000 non-hydrogen atoms;

r is 0, 1 or 2, and the sum of r and m is 3.

More preferably, in the foregoing formula, $R^1$ is a $C_{1-40}$ hydrocarbyl ligand, halohydrocarbyl or halocarbyl group.

Further preferred examples of the foregoing Lewis acid compounds are pentafluorophenylbis(pertluoronaphthyl) borane and tris(perfluoronaphthyl)borane.

Examples of preferred charge separated activating compounds according to the present invention correspond to the formula:

$$(R^1)_r\text{—B}(C_{10}F_7)_m$$

wherein:

$R^1$ each occurrence is a $C_{1-1000}$ hydrocarbyl, halohydrocarbyl, or halocarbyl group, and one $R^1$ additionally comprises a cation which is a protonated cation of a Bronsted acid, ferrocenium, a carbonium cation, a silylium cation, $Ag^+$, or the cationic derivative of a Group 3–10 metal complex catalyst;

r is 1, 2 or 3;

m is 1, 2, or 3; and the sum of r and m is 4.

More preferably, in the foregoing formula, $R^1$ is a $C_{1-40}$ hydrocarbyl ligand, halohydrocarbyl or halocarbyl group, and in one occurrence additionally comprises a tri($C_{1-40}$hydrocarbyl)ammonium cation;

Most highly preferred examples of the foregoing charge separated catalyst activators are $L^+B^-(C_6F_5)_3(C_{10}F_7)$, $L^+B^-(C_6F_5)_2(C_{10}F_7)_2$, $L^+B^-(C_6F_5)_1(C_{10}F_7)_3$, and $L^+B^-(C_{10}F_7)_4$, wherein $L^+$ is a cation of a Bronsted acid, ferrocenium, a carbonium cation, a silylium cation, $Ag^+$, or the cationic derivative of a Group 3–10 metal complex catalyst.

More preferably $L^+$ is an ammonium cation of the formula $HN^+R_3$, wherein R is $C_{1-50}$ hydrocarbyl. Most preferably, one or two R groups are $C_{14-50}$ aliphatic groups, and the remaining R group(s) is (are) $C_{1-4}$ aliphatic.

The skilled artisan will appreciate that upon activation of a metal complex to a catalytically active state by the present compounds, to the extent a cationic derivative thereof is formed, the foregoing charge separated compounds may include therein the cationic derivative of such metal complex in place of the foregoing Bronsted acid, ferrocenium, carbonium, silylium, or $Ag^+$ cations. For the preferred complexes the metal is selected from Groups 3–10 of the Periodic Table of the Elements, more preferably Group 4. Accordingly, such cationic derivative would be a Group 3–10 metal containing cation, more preferably a Group 4 metal containing cation.

Generally, solubility of the compounds of the invention in aliphatic compounds is increased by incorporation of one or more oleophilic groups such as long chain alkyl groups; long chain alkenyl groups; or halo-, alkoxy-, amino-, silyl-, or germyl- substituted long chain alkyl groups or long chain alkenyl groups into the cation, $L^+$. By the term "long chain" are meant groups having from 10 to 50 non-hydrogen atoms in such group, preferably in a non-branched form. It is understood that the catalyst activator may comprise a mixture of oleophilic groups of differing lengths in the cation. For example, one suitable activator comprises the protonated ammonium salt derived from the commercially available long chain amine comprising a mixture of two $C_{14}$, $C_{16}$ or $C_{18}$ alkyl groups and one methyl group. Such amines are available from Witco Corp., under the trade name Kemamine™ T9701, and from Akzo-Nobel under the trade name Armeen™ M2HT.

Highly preferred compounds according to the present invention are those wherein $Ar^f$ is a perfluoronaphthyl group.

Such compounds may be further illustrated by the following schematic representation of several representative neutral boron compounds where the perfluoronaphthyl group may be attached at either the α-position or the β-position. Corresponding cationic compounds contain an additional anionic ligand group of any type and a corresponding charge balancing cation.

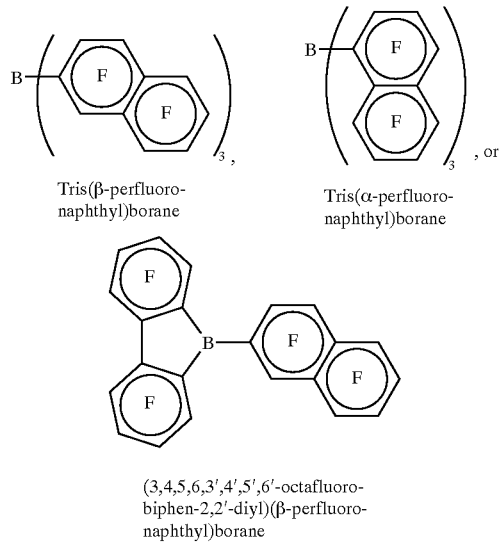

Tris(β-perfluoro-naphthyl)borane    Tris(α-perfluoro-naphthyl)borane (3,4,5,6,3',4',5',6'-octafluoro-biphen-2,2'-diyl)(β-perfluoro-naphthyl)borane wherein

represents a perfluorinated aromatic ring.

Most preferred compounds are those wherein the perfluoronaphthyl group is attached at the β-position. Examples are pentafluorophenylbis(β-perfluoronaphthyl)-borane, tris(β-perfluoronaphthyl)borane, (3,4,5,6,3',4',5',6'-octafluorobiphen-2,2'-diyl)(β-perfluoronaphthyl)borane, tri($C_{1-20}$)alkyl)ammonium salts of bis(pentafluorophenyl)-bis(β-perfluoronaphthyl)borate, tri($C_{1-20}$)alkyl)ammonium salts of pentafluorophenyl)-tris(β-perfluoronaphthyl)borate, and tri($C_{1-20}$)alkyl)ammonium salts of pentafluorophenyl)(3,4,5,6,3',4',5',6'-octafluorobiphen-2,2'-diyl)(β-perfluoronaphthyl)borate.

Suitable catalysts for use in combination with the foregoing cocatalysts include any compound or complex of a metal of Groups 3–10 of the Periodic Table of the Elements capable of being activated to polymerize ethylenically unsaturated compounds by the present activators. Examples include Group 10 diimine derivatives corresponding to the formula:

$M^*$ is Ni(II) or Pd(II);

K is halo, hydrocarbyl, or hydrocarbyloxy;

Ar* is an aryl group, especially 2,6-diisopropylphenyl or aniline group;

CT—CT is 1,2-ethanediyl, 2,3-butanediyl, or form a fused ring system wherein the two T groups together are a 1,8-naphthanediyl group; and A⁻ is the anionic component of the foregoing charge separated activators.

Similar catalysts to the foregoing are disclosed by M. Brookhart, et al., in *J. Am. Chem. Soc.*, 118, 267–268 (1996) and *J. Am. Chem. Soc.*, 117, 6414–6415 (1995), as being active polymerization catalysts especially for polymerization of α-olefins, either alone or in combination with polar comomoners such as vinyl chloride, alkyl acrylates and alkyl methacrylates.

Additional catalysts include derivatives of Group 3, 4, or Lanthanide metals which are in the +2, +3, or +4 formal oxidation state. Preferred compounds include metal complexes containing from 1 to 3 π-bonded anionic or neutral ligand groups, which may be cyclic or non-cyclic delocalized π-bonded anionic ligand groups. Exemplary of such π-bonded anionic ligand groups are conjugated or nonconjugated, cyclic or non-cyclic dienyl groups, allyl groups, boratabenzene groups, and arene groups. By the term "π-bonded" is meant that the ligand group is bonded to the transition metal by a sharing of electrons from a partially delocalized π-bond.

Each atom in the delocalized π-bonded group may independently be substituted with a radical selected from the group consisting of hydrogen, halogen, hydrocarbyl, halohydrocarbyl, hydrocarbyl-substituted metalloid radicals wherein the metalloid is selected from Group 14 of the Periodic Table of the Elements, and such hydrocarbyl- or hydrocarbyl-substituted metalloid radicals further substituted with a Group 15 or 16 hetero atom containing moiety. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system, including partially or fully hydrogenated fused ring systems, or they may form a metallocycle with the metal. Suitable hydrocarbyl-substituted organometalloid radicals include mono-, di- and tri-substituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyidimethylsilyl, methyidiethylsilyl, triphenylgermyl, and trimethylgermyl groups. Examples of Group 15 or 16 hetero atom containing moieties include amine, phosphine, ether or thioether moieties or divalent derivatives thereof, e.g. amide, phosphide, ether or thioether groups bonded to the transition metal or Lanthanide metal, and bonded to the hydrocarbyl group or to the hydrocarbyl-substituted metalloid containing group.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, and boratabenzene groups, as well as $C_{1-10}$ hydrocarbyl-substituted or $C_{1-10}$ hydrocarbyl-substituted silyl substituted derivatives thereof. Preferred anionic delocalized π-bonded groups are cyclopentadienyl, pentamethylcyclopentadienyl, tetramethylcyclopentadienyl, tetramethylsilylcyclopentadienyl, indenyl, 2,3-dimethylindenyl, fluorenyl, 2-methylindenyl, 2-methyl-4-phenylindenyl, tetrahydrofluorenyl, octahydrofluorenyl, and tetrahydroindenyl.

The boratabenzenes are anionic ligands which are boron containing analogues to benzene. They are previously known in the art having been described by G. Herberich, et al., in *Organometallics*, 14,1, 471–480 (1995). Preferred boratabenzenes correspond to the formula:

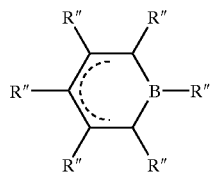

wherein R" is selected from the group consisting of hydrocarbyl, silyl, or germyl, said R" having up to 20 non-hydrogen atoms. In complexes involving divalent derivatives of such delocalized π-bonded groups one atom thereof is bonded by means of a covalent bond or a covalently bonded divalent group to another atom of the complex thereby forming a bridged system.

A suitable class of catalysts are transition metal complexes corresponding to the formula:

$$Lp_lMX_mX'_nX''_p, \text{ or a dimer thereof}$$

wherein:

Lp is an anionic, delocalized, π-bonded group that is bound to M, containing up to 50 non-hydrogen atoms, optionally two Lp groups may be joined together forming a bridged structure, and further optionally one Lp may be bound to X;

M is a metal of Group 4 of the Periodic Table of the Elements in the +2, +3 or +4 formal oxidation state;

X is an optional, divalent substituent of up to 50 non-hydrogen atoms that together with Lp forms a metallocycle with M;

X' is an optional neutral ligand having up to 20 non-hydrogen atoms;

X" each occurrence is a monovalent, anionic moiety having up to 40 non-hydrogen atoms, optionally, two X" groups may be covalently bound together forming a divalent dianionic moiety having both valences bound to M, or, optionally 2 X" groups may be covalently bound together to form a neutral, conjugated or nonconjugated diene that is π-bonded to M (whereupon M is in the +2 oxidation state), or further optionally one or more X" and one or more X' groups may be bonded together thereby forming a moiety that is both covalently bound to M and coordinated thereto by means of Lewis base functionality;

l is 0, 1 or 2;

m is 0 or 1;

n is a number from 0 to 3;

p is an integer from 0 to 3; and the sum, l+m+p, is equal to the formal oxidation state of M, except when 2 X" groups together form a neutral conjugated or non-conjugated diene that is π-bonded to M, in which case the sum l+m is equal to the formal oxidation state of M.

Preferred complexes include those containing either one or two Lp groups. The latter complexes include those containing a bridging group linking the two Lp groups. Preferred bridging groups are those corresponding to the formula $(ER^*_2)_x$ wherein E is silicon, germanium, tin, or carbon, R* independently each occurrence is hydrogen or a group selected from silyl, hydrocarbyl, hydrocarbyloxy and combinations thereof, said R* having up to 30 carbon or silicon atoms, and x is 1 to 8. Preferably, R* independently each occurrence is methyl, ethyl, propyl, benzyl, tert-butyl, phenyl, methoxy, ethoxy or phenoxy.

Examples of the complexes containing two Lp groups are compounds corresponding to the formula:

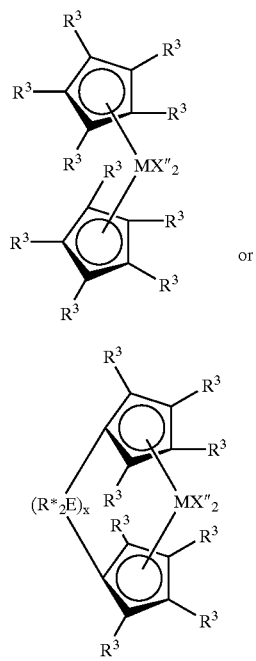

wherein:
M is titanium, zirconium or hafnium, preferably zirconium or hafnium, in the +2 or +4 formal oxidation state;
$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system, and
X" independently each occurrence is an anionic ligand group of up to 40 non-hydrogen atoms, or two X" groups together form a divalent anionic ligand group of up to 40 non-hydrogen atoms or together are a conjugated diene having from 4 to 30 non-hydrogen atoms forming a π-complex with M, whereupon M is in the +2 formal oxidation state, and
R*, E and x are as previously defined.

The foregoing metal complexes are especially suited for the preparation of polymers having stereoregular molecular structure. In such capacity it is preferred that the complex possesses $C_s$ symmetry or possesses a chiral, stereorigid structure. Examples of the first type are compounds possessing different delocalized π-bonded systems, such as one cyclopentadienyl group and one fluorenyl group. Similar systems based on Ti(IV) or Zr(IV) were disclosed for preparation of syndiotactic olefin polymers in Ewen, et al., J. Am. Chem. Soc. 110, 6255–6256 (1980). Examples of chiral structures include rac bis-indenyl complexes. Similar systems based on Ti(IV) or Zr(IV) were disclosed for preparation of isotactic olefin polymers in Wild et al., J. Organomet. Chem., 232, 233–47, (1982).

Exemplary bridged ligands containing two π-bonded groups are:
dimethylbis(cyclopentadienyl)silane, dimethylbis(tetramethylcyclopentadienyl)silane,
dimethylbis(2-ethylcyclopentadien-1-yl)silane, dimethylbis(2-t-butylcyclopentadien-1-yl)silane,
2,2-bis(tetramethylcyclopentadienyl)propane, dimethylbis(inden-1-yl)silane,
dimethylbis(tetrahydroinden-1-yl)silane, dimethylbis(fluoren-1-yl)silane,
dimethylbis(tetrahydrofluoren-1-yl)silane, dimethylbis(2-methyl-4-phenylinden-1-yl)-silane,
dimethylbis(2-methylinden-1-yl)silane, dimethyl(cyclopentadienyl)(fluoren-1-yl)silane,
dimethyl(cyclopentadienyl)(octahydrofluoren-1-yl)silane,
dimethyl(cyclopentadienyl)(tetrahydrofluoren-1-yl)silane,
(1, 1, 2, 2-tetramethy)-1, 2-bis(cyclopentadienyl)disilane,
(1, 2-bis(cyclopentadienyl)ethane, and
dimethyl(cyclopentadienyl)-1-(fluoren-1-yl)methane.

Preferred X" groups are selected from hydride, hydrocarbyl, silyl, germyl, halohydrocarbyl, halosilyl, silylhydrocarbyl and aminohydrocarbyl groups, or two X" groups together form a divalent derivative of a conjugated diene or else together they form a neutral, π-bonded, conjugated diene. Most preferred X" groups are $C_{1-20}$ hydrocarbyl groups.

A further class of metal complexes utilized in the present invention corresponds to the preceding formula $Lp_lMX_mX'_nX''_p$, or a dimer thereof, wherein X is a divalent substituent of up to 50 non-hydrogen atoms that together with Lp forms a metallocycle with M.

Preferred divalent X substituents include groups containing up to 30 non-hydrogen atoms comprising at least one atom that is oxygen, sulfur, boron or a member of Group 14 of the Periodic Table of the Elements directly attached to the delocalized π-bonded group, and a different atom, selected from the group consisting of nitrogen, phosphorus, oxygen or sulfur that is covalently bonded to M.

A preferred class of such Group 4 metal coordination complexes used according to the present invention corresponds to the formula:

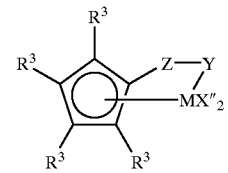

wherein:
M is titanium or zirconium, preferably titanium in the +2, +3, or +4 formal oxidation state;
$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system,
each X" is a halo, hydrocarbyl, hydrocarbyloxy or silyl group, said group having up to 20 non-hydrogen atoms, or two X" groups together form a neutral $C_{5-30}$ conjugated diene or a divalent derivative thereof;
Y is —O—, —S—, —NR*—, —PR*—; and
Z is $SiR*_2$, $CR*_2$, $SiR*_2SiR*_2$, $CR*_2CR*_2$, $CR*=CR*$, $CR*_2SiR*_2$, or $GeR*_2$, wherein R* is as previously defined.

Illustrative Group 4 metal complexes that may be employed in the practice of the present invention include:
cyclopentadienyltitaniumtrimethyl,
cyclopentadienyltitaniumtriethyl,
cyclopentadienyltitaniumtriisopropyl, cyclopentadienyltitaniumtriphenyl,
cyclopentadienyltitaniumtribenzyl,
cyclopentadienyltitanium-2,4-dimethylpentadienyl,
cyclopentadienyltitanium-2,4-dimethylpentadienyl·triethylphosphine,
cyclopentadienyltitanium-2,4-dimethylpentadienyl·trimethylphosphine,
cyclopentadienyltitaniumdimethylmethoxide,
cyclopentadienyltitaniumdimethylchloride,
pentamethylcyclopentadienyltitaniumtrimethyl,
indenyltitaniumtrimethyl,
indenyltianiumtriethyl,
indenyltitaniumtripropyl,
indenyltitaniumtriphenyl,
tetrahydroindenyltitaniumtribenzyl,
pentamethylcyclopentadienyltitaniumtriisopropyl,
pentamethylcyclopentadienyltitaniumtribenzyl,
pentamethylcyclopentadienyltitaniumdimethylmethoxide,
pentamethylcyclopentadienyltitaniumdimethylchloride,
bis($\eta^5$-2,4-dimethylpentadienyl)titanium,
bis($\eta^5$-2,4-dimethylpentadienyl)titanium·trimethylphosphine,
bis($\eta^5$-2,4-dimethylpentadienyl)titanium·triethylphosphine,
octahydrofluorenyltitaniumtrimethyl,
tetrahydroindenyltitaniumtrimethyl,
tetrahydrofluorenyltitaniumtrimethyl,
(tert-butylamido)(1,1-dimethyl-2,3,4,9,10-$\eta$-1,4,5,6,7,8-hexahydronaphthalenyl)dimethylsilanetitaniumdimethyl,
(tert-butylamido)(1,1,2,3-tetramethyl-2,3,4,9,10-$\eta$-1,4,5,6,7,8-hexahydronaphthalenyl)dimethylsilanetitaniumdimethyl,
(tert-butylamido)(tetramethyl-$\eta^5$-cyclopentadienyl)dimethylsilanetitanium dibenzyl,
(tert-butylamido)(tetramethyl-$\eta^5$-cyclopentadienyl)dimethylsilanetitanium dimethyl,
(tert-butylamido)(tetramethyl-$\eta^5$-cyclopentadienyl)-1,2-ethanediyltitanium dimethyl,
(tert-butylamido)(tetramethyl-$\eta^5$-indenyl)dimethylsilanetitanium dimethyl,
(tert-butylamido)(tetramethyl-$\eta^5$-cyclopentadienyl) dimethylsilane titanium (III) 2-(dimethylamino)benzyl;
(tert-butylamido)(tetramethyl-$\eta^5$-cyclopentadienyl) dimethylsilanetitanium (III) allyl,
(tert-butylamido)(tetramethyl-$\eta^5$-cyclopentadienyl) dimethylsilanetitanium (III) 2,4-dimethylpentadienyl,
(tert-butylamido)(tetramethyl-$\eta^5$-cyclopentadienyl) dimethylsilanetitanium (II) 1,4-diphenyl-1,3-butadiene,
(tert-butylamido)(tetramethyl-$\eta^5$-cyclopentadienyl) dimethylsilanetitanium (II) 1,3-pentadiene,
(tert-butylamido)(2-methylindenyl)dimethylsilanetitanium (II) 1,4-diphenyl-1,3-butadiene,
(tert-butylamido)(2-methylindenyl)dimethylsilanetitanium (II) 2,4-hexadiene,
(tert-butylamido)(2-methylindenyl)dimethylsilanetitanium (IV) 2,3-dimethyl-1,3-butadiene,
(tert-butyiamido)(2-methylindenyl)dimethylsilanetitanium (IV) isoprene,
(tert-butylamido)(2-methylindenyl)dimethylsilanetitanium (IV) 1,3-butadiene,
(tert-butylamido)(2,3-dimethylindenyl)dimethylsitanetitanium (IV) 2,3-dimethyl-1,3-butadiene,
(tert-butylamido)(2,3-dimethylindenyl)dimethylsilanetitanium (IV) isoprene
(tert-butylamido)(2,3-dimethylindenyl)dimethylsilanetitanium (IV) dimethyl
(tert-butylamido)(2,3-dimethylindenyl)dimethylsilanetitanium (IV) dibenzyl
(tert-butylamido)(2,3-dimethylindenyl)dimethylsilanetitanium (IV) 1,3-butadiene,
(tert-butylamido)(2,3-dimethylindenyl)dimethylsilanetitanium (II) 1,3-pentadiene,
(tert-butylamido)(2,3-dimethylindenyl)dimethylsilanetitanium (II) 1,4-diphenyl-1,3-butadiene,
(tert-butylamido)(2-methylindenyl)dimethylsilanetitanium (II) 1,3-pentadiene,
(tert-butylamido)(2-methylindenyl)dimethylsilanetitanium (IV) dimethyl,
(tert-butylamido)(2-methylindenyl)dimethylsilanetitanium (IV) dibenzyl,
(tert-butylamido)(2-methyl-4-phenylindenyl) dimethylsilanetitanium (II) 1,4-diphenyl-1,3-butadiene,
(tert-butylamido)(2-methyl-4-phenylindenyl) dimethylsilanetitanium (II) 1,3-pentadiene,
(tert-butylamido)(2-methyl-4-phenylindenyl) dimethylsilanetitanium (II) 2,4-hexadiene,
(tert-butylamido)(tetramethyl-$\eta^5$-cyclopentadienyl) dimethyl-silanetitanium (IV)1,3-butadiene,
(tert-butylamido)(tetramethyl-$\eta^5$-cyclopentadienyl) dimethylsilanetitanium (IV) 2,3-dimethyl-1,3-butadiene,
(tert-butylamido)(tetramethyl-$\eta^5$-cyclopentadienyl) dimethylsilanetitanium (IV) isoprene,
(tert-butylamido)(tetramethyl-$\eta^5$-cyclopentadienyl) dimethyl-silanetitanium (II) 1,4-dibenzyl-1,3-butadiene,
(tert-butylamido)(tetramethyl-$\eta^5$-cyclopentadienyl) dimethylsilanetitanium (II) 2,4-hexadiene,
(tert-butylamido)(tetramethyl-$\eta^5$-cyclopentadienyl) dimethylsilanetitanium (II) 3-methyl-1,3-pentadiene,
(tert-butylamido)(2,4-dimethyipentadien-3-yl) dimethylsilanetitaniumdimethyl,
(tert-butylamido)(6,6-dimethyicyclohexadienyl) dimethylsilanetitaniumdimethyl,
(tert-butylamido)(1,1-dimethyl-2,3,4,9,10-$\eta$-1,4,5,6,7,8-hexahydronaphthalen-4-yl)dimethylsilanetitaniumdimethyl,
(tert-butylamido)(1,1,2,3-tetramethyl-2,3,4,9,10-$\eta$-1,4,5,6,7,8-hexahydronaphthalen-4-yl)dimethylsilanetitaniumdimethyl
(tert-butylamido)(tetramethyl-$\eta^5$-cyclopentadienyl methylphenylsilanetitanium (IV) dimethyl,
(tert-butylamido)(tetramethyl-$\eta^5$-cyclopentadienyl methylphenylsilanetitanium (II) 1,4-diphenyl-1,3-butadiene,
1-(tert-butylamido)-2-(tetramethyl-$\eta^5$-cyclopentadienyl) ethanediyltitanium (IV) dimethyl, and
1-(tert-butylamido)-2-(tetramethyl-$\eta^5$-cyclopentadienyl) ethanediyl-titanium (II) 1,4-diphenyl-1,3-butadiene.

Complexes containing two Lp groups including bridged complexes suitable for use in the present invention include:
bis(cyclopentadienyl)zirconiumdimethyl,
bis(cyclopentadienyl)zirconium dibenzyl,
bis(cyclopentadienyl)zirconium methyl benzyl,
bis(cyclopentadienyl)zirconium methyl phenyl,
bis(cyclopentadienyl)zirconiumdiphenyl,
bis(cyclopentadienyl)titanium-allyl,
bis(cyclopentadienyl)zirconiummethylmethoxide, bis(cyclopentadienyl)zirconiummethylchloride,
bis(pentamethylcyclopentadienyl)zirconiumdimethyl,
bis(pentamethylcyclopentadienyl)titaniumdimethyl,
bis(indenyl)zirconiumdimethyl,
indenylfluorenylzirconiumdimethyl,
bis(indenyl)zirconiummethyl(2-(dimethylamino)benzyl),
bis(indenyl)zirconiummethyltrimethylsilyl,
bis(tetrahydroindenyl)zirconiummethyltrimethylsilyl,
bis(pentamethylcyclopentadienyl)zirconiummethylbenzyl,
bis(pentamethylcyclopentadienyl)zirconiumdibenzyl, bis(pentamethylcyclopentadienyl)zirconiummethyl-
methoxide,
bis(pentamethylcyclopentadienyl)zirconiummethyl-
chloxide,
bis(methylethylcyclopentadienyl)zirconiumdimethyl,
bis(butylcyclopentadienyl)zirconiumdibenzyl,
bis(t-butylcyclopentadienyl)zirconiumdimethyl,
bis(ethyltetramethylcyclopentadienyl)zirconiumdimethyl,
bis(methylpropylcyclopentadienyl)zirconiumdibenzyl,
bis(trimethylsilylcyclopentadienyl)zirconiumdibenzyl,
dimethyrsilylsbis(cyclopentadienyl)zirconiumdimethyl,
dimethylsilyl-bis(tetramethylcyclopentadienyl)titanium (III) allyl
dimethylsilyl-bis(t-butylcyclopentadienyl) zirconiumdichloride,
dimethylsilyl-bis(n-butylcyclopentadienyl) zirconiumdichloride,
(methylene-bis(tetramethylcyclopentadienyl)titanium(III) 2-(dimethylamino)benzyl,
(methylene-bis(n-butylcyclopentadienyl)titanium(III) 2-(dimethylamino)benzyl,
dimethylsilyl-bis(indenyl)zirconiumbenzylchloride,
dimethylsilyl-bis(2-methylindenyl)zirconiumdimethyl,
dimethylsilyl-bis(2-methyl-4-phenylindenyl) zirconiumdimethyl,
dimethylsilyl-bis(2-methylindenyl)zirconium-1,4-diphenyl-1,3-butadiene,
dimethylsilyl-bis(2-methyl-4-phenylindenyl)zirconium (II) 1,4-diphenyl-1,3-butadiene,
dimethylsilyl-bis(tetrahydroindenyl)zirconium(II) 1,4-diphenyl-1,3-butadiene,
dimethylsilyl-bis(fluorenyl)zirconiummethylchloride,
dimethylsilyl-bis(tetrahydrofluorenyl)zirconium bis (trimethylsilyl),
(isopropylidene)(cyclopentadienyl)(fluorenyl) zirconiumdibenzyl, and
dimethylsilyl(tetramethylcyclopentadienyl)(fluorenyl) zirconium dimethyl.

Other catalysts, especially catalysts containing other Group 4 metals, will, of course, be apparent to those skilled in the art.

The cocatalysts of the invention may also be used in combination with a an oligomeric or polymeric alumoxane compound, a tri(hydrocarbyl)aluminum compound, a di(hydrocarbyl)(hydrocarbyloxy)aluminum compound, a di(hydrocarbyl)(dihydrocarbyl-amido)aluminum compound, a bis(dihydrocarbyl-amido)(hydrocarbyl) aluminum compound, a di(hydrocarbyl)amido(disilyl) aluminum compound, a di(hydrocarbyl)-amido (hydrocarbyl)(silyl)aluminum compound, a bis (dihydrocarbylamido)(silyl)aluminum compound, or a mixture of the foregoing compounds, having from 1 to 20 non-hydrogen atoms in each hydrocarbyl, hydrocarbyloxy, or silyl group, if desired. These aluminum compounds are usefully employed for their beneficial ability to scavenge impurities such as oxygen, water, and aldehydes from the polymerization mixture.

Preferred aluminum compounds include $C_{2-6}$ trialkyl aluminum compounds, especially those wherein the alkyl groups are ethyl, propyl, isopropyl, n-butyl, isobutyl, pentyl, neopentyl, or isopentyl, dialkyl(aryloxy)aluminum compounds containing from 1–6 carbons in the alkyl group and from 6 to 18 carbons in the aryl group (especially (3,5-di (t-butyl)-4-methylphenoxy)diisobutylaluminum), methylalumoxane, modified methylalumoxane and diisobutylalumoxane. The molar ratio of aluminum compound to metal complex is preferably from 1:10,000 to 1000:1, more preferably from 1:5000 to 100:1, most preferably from 1:100 to 100:1.

The molar ratio of catalyst/cocatalyst employed preferably ranges from 1:10 to 10:1, more preferably from 1:5 to 1:1, most preferably from 1:1.5 to 1:1. Mixtures of the activating cocatalysts of the present invention may also be employed if desired.

Suitable addition polymerizable monomers include ethylenically unsaturated monomers, acetylenic compounds, conjugated or non-conjugated dienes, and polyenes. Preferred monomers include olefins, for examples alpha-olefins having from 2 to 20,000, preferably from 2 to 20, more preferably from 2 to 8 carbon atoms and combinations of two or more of such alpha-olefins. Particularly suitable alpha-olefins include, for example, ethylene, propylene, 1-butene, 1-pentene, 4-methylpentene-1, 1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{10-30}$ α-olefins specifically added to the reaction mixture in order to produce relatively long chain branches in the resulting polymers. Preferably, the alpha-olefins are ethylene, propene, 1-butene, 4-methyl-pentene-1, 1-hexene, 1-octene, and combinations of ethylene and/or propene with one or more of such other alpha-olefins. Other preferred monomers include styrene, halo- or alkyl substituted styrenes, tetrafluoroethylene, vinylcyclobutene, 1,4-hexadiene, dicyclopentadiene, ethylidene norbornene, and 1,7-octadiene. Mixtures of the above-mentioned monomers may also be employed.

In general, the polymerization may be accomplished under conditions well known in the prior art for Ziegler-Natta or Kaminsky-Sinn type polymerization reactions. Suspension, solution, slurry, gas phase or high pressure, whether employed in batch or continuous form or other process conditions, may be employed if desired. Examples of such well known polymerization processes are depicted in WO 88/02009, U.S. Pat. Nos. 5,084,534, 5,405,922, 4,588, 790, 5,032,652, 4,543,399, 4,564,647, 4,522,987, and elsewhere. Preferred polymerization temperatures are from 0–250° C. Preferred polymerization pressures are from atmospheric to 3000 atmospheres.

Preferred processing conditions include solution polymerization, more preferably continuous solution polymerization processes, conducted in the presence of an aliphatic or alicyclic liquid diluent. By the term "continuous polymerization" is meant that at least the products of the polymerization are continuously removed from the reaction mixture, such as for example by devolatilization of a portion of the reaction mixture. Preferably one or more reactants are also continuously added to the polymerization mixture during the polymerization. Examples of suitable aliphatic or alicyclic liquid diluents include straight and branched-chain hydrocarbons such as isobutane, butane, pentane, hexane, heptane, octane, and mixtures thereof; alicyclic hydrocarbons such as cyclohexane, cycloheptane, methylcyclohexane, methylcycloheptane, and mixtures thereof; and perfluorinated hydrocarbons such as perfluorinated $C_{4-10}$ alkanes. Suitable diluents also include aromatic hydrocarbons (particularly for use with aromatic α-olefins such as styrene or ring alkyl-substituted styrenes) including toluene, ethylbenzene or xylene, as well as liquid olefins (which may act as monomers or comonomers) including ethylene, propylene, butadiene, cyclopentene, 1-hexene, 3-methyl-1-pentene, 4-methyl-1-pentene, 1,4-hexadiene, 1-octene, 1-decene, styrene, divinylbenzene, allylbenzene, vinyltoluene (including all isomers alone or in admixture). Mixtures of the foregoing are also suitable.

In most polymerization reactions the molar ratio of catalyst:polymerizable compounds employed is from $10^{-12}:1$ to $10^{-1}:1$, more preferably from $10^{-12}:1$ to $10^{-5}:1$.

The catalyst composition of the invention may also be utilized in combination with at least one additional homogeneous or heterogeneous polymerization catalyst in separate reactors connected in series or in parallel to prepare polymer blends having desirable properties. An example of such a process is disclosed in WO 94/00500, equivalent to U.S. Ser. No. 07/904,770, now abandoned. A more specific process is disclosed in copending application U.S. Ser. No. 08/10958, filed Jan. 29, 1993, now abandoned.

Molecular weight control agents can be used in combination with the present cocatalysts. Examples of such molecular weight control agents include hydrogen, trialkyl aluminum compounds or other known chain transfer agents. A particular benefit of the use of the present cocatalysts is the ability (depending on reaction conditions) to produce narrow molecular weight distribution α-olefin homopolymers and copolymers in greatly improved catalyst efficiencies. Preferred polymers have Mw/Mn of less than 2.5, more preferably less than 2.3. Such narrow molecular weight distribution polymer products are highly desirable due to improved tensile strength properties.

The catalyst composition of the present invention can also be employed to advantage in the gas phase polymerization and copolymerization of olefins. Gas phase processes for the polymerization of olefins, especially the homopolymerization and copolymerization of ethylene and propylene, and the copolymerization of ethylene with higher alpha olefins such as, for example, 1-butene, 1-hexene, 4-methyl-1-pentene are well known in the art. Such processes are used commercially on a large scale for the manufacture of high density polyethylene (HDPE), medium density polyethylene (MDPE), linear low density polyethylene (LLDPE) and polypropylene.

The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported above a perforated plate, the fluidisation grid, by a flow of fluidisation gas.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a wider diameter than the fluidized bed and wherein fine particles entrained in the gas stream have an opportunity to gravitate back into the bed. It can also be advantageous to use a cyclone to remove ultra-fine particles from the hot gas stream. The gas is then normally recycled to the bed by means of a blower or compressor and a one or more heat exchangers to strip the gas of the heat of polymerization.

A preferred method of cooling of the bed, in addition to the cooling provided by the cooled recycle gas, is to feed a volatile liquid to the bed to provide an evaporative cooling effect. The volatile liquid employed in this case can be, for example, a volatile inert liquid, for example, a saturated hydrocarbon having 3 to 8, preferably 4 to 6, carbon atoms. In the case that the monomer or comonomer itself is a volatile liquid, or can be condensed to provide such a liquid this can be suitably be fed to the bed to provide an evaporative cooling effect. Examples of olefin monomers which can be employed in this manner are olefins containing from 3 to eight, preferably from 3 to six carbon atoms. The volatile liquid evaporates in the hot fluidized bed to form gas which mixes with the fluidizing gas. If the volatile liquid is a monomer or comonomer, it will undergo some polymerization in the bed. The evaporated liquid then emerges from the reactor as part of the hot recycle gas, and enters the compression/heat exchange part of the recycle loop. The recycle gas is cooled in the heat exchanger and, if the temperature to which the gas is cooled is below the dew point, liquid will precipitate from the gas. This liquid is desirably recycled continuously to the fluidized bed. It is possible to recycle the precipitated liquid to the bed as liquid droplets carried in the recycle gas stream, as described, for example, in EP-A-89691, U.S. Pat. No. 4,543,399, WO 94/25495 and U.S. Pat. No. 5352749. A particularly preferred method of recycling the liquid to the bed is to separate the liquid from the recycle gas stream and to reinject this liquid directly into the bed, preferably using a method which generates fine droplets of the liquid within the bed. This type of process is described in WO 94/28032.

The polymerization reaction occurring in the gas fluidized bed is catalyzed by the continuous or semi-continuous addition of catalyst. Such catalysts can be supported on an inorganic or organic support material if desired. The catalyst can also be subjected to a prepolymerization step, for example, by polymerizing a small quantity of olefin monomer in a liquid inert diluent, to provide a catalyst composite comprising catalyst particles embedded in olefin polymer particles.

The polymer is produced directly in the fluidized bed by catalyzed (co)polymerization of the monomer(s) on the fluidized particles of catalyst, supported catalyst or prepolymer within the bed. Start-up of the polymerization reaction is achieved using a bed of preformed polymer particles, which, preferably, is similar to the target polyolefin, and conditioning the bed by drying with inert gas or nitrogen prior to introducing the catalyst, the monomer(s) and any other gases which it is desired to have in the recycle gas stream, such as a diluent gas, hydrogen chain transfer agent, or an inert condensable gas when operating in gas phase condensing mode. The produced polymer is discharged continuously or discontinuously from the fluidized bed as desired, optionally exposed to a catalyst kill and optionally pelletized.

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis.

EXAMPLE 1

Preparation of Tris(β-Perfluoronaphthyl)borane

The starting material, 2-perfluoronaphthylhydrazine, was synthesized by a modification of the procedure of Gething, et al., *J. Chem. Soc.*, 36, 186 (1962). Octafluornaphthalene, hydrazine hydrate, and ethanol were mixed and refluxed. The reaction was quenched by addition of cold water when the ratio between 2-perfluoronaphthylhydrazine and octafluoronaphthalene reached 97:3, which gave the best yield. The organic products were extracted with $CH_2Cl_2$ and the extracts were combined and dried over $MgSO_4$, filtered and evaporated to leave a brown solid. After removing unreacted octafluoronaphthalene and byproducts by sublimation at room temperature, the brown solid remaining exhibited a clean $^{19}$F NMR spectrum of 2-perfluoronaphthylhydrazine.

The above brown solid was used directly for the synthesis of 2-bromoheptafluoronaphthalene using a modification of the procedure of Brooke, et al., *J. Fluorine Chemistry*, 50, 229, (1990). Thus, 2-perfluoronaphthylhydrazine, copper(II) bromide and hydribromic acid were heated together under reflux for 1 h. The mixture was then filtered after the solution was cooled to room temperature. The residual solid was washed with water and then extracted with methylene chloride. The solution was next dried over MgSO$_4$, filtered, and evaporated to leave a brown solid. Sublimation gave pure 2-bromoheptafluoro-naphthalene. Yield, 51 percent.

In a 250-mL flask, 2-bromoheptafluoronaphthalene (3.0 g, 9.0 mmol) was dissolved in 85 mL dry pentane. The solution was stirred at −30° C. for 10 min. and then 5.63 mL of n-butyllithium (1.6 M in hexanes, 9.0 mmol) was added dropwise by syringe. A white precipitate formed immediately. The solution was stirred between −40° C. and −30° C. for 1 h and 20 min after the addition. Next 3.0 mL of BCl$_3$ (1.0 M in hexanes, 3.0 mmol) was then added quickly at −40° C. The solution turned yellow at once and was allowed to warm slowly to room temperature overnight. All the volatiles were then removed in vacuo to give a yellow solid. Sublimation at 150° C. (0.05 mmHg) for 3 h removed yellow, sticky byproducts. Next, the sublimation at 220° C. (0.05 mmHg) for 3 h gave analytically pure 0.6 g tris (β-perfluoronaphthyl)borane. Yield, 26 percent.

$^{19}$F NMR (C$_6$D$_6$, 23° C., 282.330 MHz): δ−102.97 (dd, 3F, F-1, $^4J_{F_1-F_8}$=73.12 Hz, $^4J_{F_1-F_3}$=18.35 Hz), −129.66 (d, 3F, F-3, $^4J_{F_3-F_1}$=18.35 Hz), −142.04 (dt, 3F, F-8, $^4J_{F_8-F_1}$=73.12 Hz, $^3J_{F_8-F_7}$=16.80 Hz), −145.18 (dt, 3F, F-5, $^4J_{F_5-F_4}$=57.88 Hz, $^3J_{F_5-F_6}$=16.80 Hz), −149.33 (dt, 3F, F-4, $^4J_{F_4-F_5}$=57.88 Hz, $^3J_{F_4-F_3}$=18.21 Hz), −149.60 (t, br, 3F, F-6, $^3J_{F_6-F_7}$=21.46 Hz), −155.09 (t, br, 3F, F-7, $^3J_{F_7-F_8}$=16.80 Hz).

MS: parent ion at m/e 770.

Anal. Calcd for C$_{30}$BF$_{21}$: C, 46.79; H, 0.00; N, 0.00. Found: C, 46.91, H, 0.07, N, 0.00.

Synthesis of Bis(dimethylcyclopentadienyl) zirconium Methyl Tris(β-perfluoronaphthyl) methylborate [(C$_5$H$_3$(CH$_3$)$_2$)$_2$ZrCH$_3$]$^+$[CH$_3$(C$_{10}$F$_7$)$_3$B]$^-$-(A)

Bis(dimethylcyclopentadienyl)zirconium dimethyl (4.6 mg, 0.015 mmol) and tris (β-perfluoronaphthyl)borane (11.6 mg, 0.015 mmol) were dissolved in the C$_6$D$_6$ in a J-Young NMR tube. The reaction occurred immediately to give bis(dimethylcyclopentadienyl)zirconium methyltris(β-perfluoronaphthyl)methylborate and a byproduct, a μ-F bridged dimeric cationic species: {[(C$_5$H$_3$(CH$_3$)$_2$)$_2$ZrMe]$_2$(μ-F)}$^+$[CH$_3$(C$_{10}$F$_7$)$_3$B]$^-$ in a ratio of 7:1. bis(dimethylcyclorentadienyl)zirconium methyltris(β-perfluoronaphthyl)methylborate analysis $^1$H NMR (C$_6$D$_6$, 23° C., 299.910 MHz): δ 5.82 (t, 2H, C$_5$H$_3$Me$_2$, $^3J_{H-H}$=2.6 Hz), 5.47 (t, 2H, C$_5$H$_3$Me$_2$, $^3J_{H-H}$=3.0 Hz), 4.88 (t, 2H, C$_5$H$_3$Me$_2$, $^3J_{H-H}$=2.7 Hz), 1.68 (s, 6H, C$_5$H$_3$Me$_2$), 1.24 (s, 6H, C$_5$H$_3$Me$_2$), 0.44(s, br, 3H, B—CH$_3$), 0.20 (s, 3H, Zr—CH$_3$).

$^{19}$F NMR (C$_6$D$_6$, 23° C., 282.330 MHz): δ −110.40 (dd, 3F, F-1, $^4J_{F_1-F_8}$=73.12 Hz, $^4J_{F_1-F_3}$=15.53 Hz), −127.22 (d, br, 3F, F-3), −146.28 (dt, 3F, F-8, $^4J_{F_8-F_7}$=76.23 Hz, $^3J_{F_8-F_7}$=16.80 Hz), −146.77 (dt, 3F, F-5, $^4J_{F_5-F_4}$=54.77 Hz, $^3J_{F_5-F_6}$=16.80 Hz), −152.59 (dt, 3F, F-4, $^4J_{F_4-F_5}$=55.05 Hz, $^3J_{F_4-F_3}$=18.35 Hz), −157.12 (t, br, 3F, F-6, $^3J_{F_6-F_7}$=19.76 Hz), −158.53 (t, br, 3F, F-7, $^3J_{F_7-F_8}$=18.35 Hz).

{[(C$_5$H$_3$(CH$_3$)$_2$)$_2$ZrMe]$_2$(μ-F)}$^+$[CH$_3$(C$_{10}$F$_7$)$_3$B]$^-$ analysis:

$^1$H NMR (C$_6$D$_6$, 23° C., 299.910 MHz): δ 5.61 (td, 4H, C$_5$H$_3$Me$_2$, $^3J_{H-H}$=2.7 Hz, $^3J_{H-F}$=1.1 Hz), 5.28 (dd, 4H, C$_5$H$_3$Me$_2$, $^3J_{H-H}$=3.3 Hz), 5.16 (t, 4H, C$_5$H$_3$Me$_2$, $^3J_{H-H}$=2.7 Hz), 1.66 (s, br, 3H, B—CH$_3$), 1.64 (s, 12H, C$_5$H$_3$Me$_2$), 1.36 (s, 12H, C$_5$H$_3$Me$_2$), 0.04 (s, 6H, Zr—CH$_3$, $^3J_{H-F}$=2.1 Hz).

$^{19}$F NMR (C$_6$D$_6$, 23° C., 282.330 MHz): δ −91.20 (s, 1F, Zr—F—Zr), −108.42 (dd, 3F, F-1, $^4J_{F_1-F_8}$=73.41 Hz, $^4J_{F_1-F_3}$=15.25 Hz), −123.76 (d, br, 3F, F-3, $^4J_{F_1-F_3}$=15.25 Hz −145.95 (dt, 3F, F-8, $^4J_{F_8-F_1}$=76.23 Hz, $^3J_{F_8-F_7}$=16.80 Hz), −149.89 (dt, 3F, F-5, $^4J_{F_5-F_4}$=54.77 Hz, $^3J_{F_5-F_6}$=16.80 Hz), −155.34 (dt, 3F, F-4, $^4J_{F_4-F_5}$=54.77 Hz, $^3J_{F_4-F_3}$=19.76 Hz), −160.96 (t, br, 3F, F-6, $^3J_{F_6-F_7_5}$=18.35 Hz), −161.87 (t, br, 3F, F-7, $^3J_{F_7-F_8}$=18.35 Hz).

Synthesis of (μ-Me) dimer salt: {[(C$_5$H$_3$(CH$_3$)$_2$)$_2$ZrMe]$_2$(μ-Me)}$^+$[CH$_3$(C$_{10}$F$_7$)$_3$B]$^-$-(B)

Bis(dimethylcyclopentadienyl)zirconiumdimethyl (9.2 mg, 0.030 mmol) and tris(β-perfluoronaphthyl)methylborane (11.6 mg, 0.015 mmol) were dissolved in the C$_6$D$_6$ in a J-Young NMR tube. The reaction occurred immediately to give {[(C$_5$H$_3$(CH$_3$)$_2$)$_2$ZrMe]$_2$(μ-Me)}$^{+[CH_3}$(C$_{10}$F$_7$)$_3$B]$^-$ and the byproduct, μ-F bridged dimeric cationic species {[(C$_5$H$_3$(CH$_3$)$_2$)$_2$ZrMe]$_2$(μ-F)}$^+$[CH$_3$(C$_{10}$F$_7$)$_3$B]$^-$ (3b) in a ratio of 5:1 {[(C$_5$H$_3$(CH$_3$)$_2$)$_2$ZrMe]$_2$(μ-Me)}$^+$[CH$_3$(C$_{10}$F$_7$)$_3$B]$^-$ analysis:

$^1$H NMR (C$_6$D$_6$, 23° C., 299.910 MHz): δ 5.44 (t, 4H, C$_5$H$_3$Me$_2$, $^3J_{H-H}$=2.7 Hz), 5.40 (t, 4H, C$_5$H$_3$Me$_2$, $^3J_{H-H}$=3.3 Hz), 5.11 (t, 4H, C$_5$H$_3$Me$_2$, $^3J_{H-H}$=2.7 Hz), 1.66 (s, 12H, C$_5$H$_3$Me$_2$), 1.45 (s, 12H, C$_5$H$_3$Me$_2$), 1.65 (s, br, 3H, B—CH$_3$), −0.32 (s, 6H, Zr—CH$_3$), −1.59 (s, 3H, Zr—CH$_3$—Zr).

$^{13}$C NMR (C$_6$D$_6$, 23° C.): δ 126.01 (s, C$_5$H$_3$Me$_2$), 125.63 (s, C$_5$H$_3$Me$_2$), 113.92 (s, C$_5$H$_3$Me$_2$), 111.38 (s, C$_5$H$_3$Me$_2$), 106.46 (s, C$_5$H$_3$Me$_2$), 41.77 (s, Zr—CH$_3$), 22.58 (s, B—CH$_3$), 22.34 (s, Zr—CH$_3$—Zr), 12.93 (s, C$_5$H$_3$Me$_2$), 12.66 (s, C$_5$H$_3$Me$_2$).

$^{19}$F NMR (C$_6$D$_6$, 23° C., 282.330 MHz): δ −108.42 (dd, 3F, F-1, $^4J_{F_1-F_8}$=73.41 Hz, $^4J_{F_1-3}$=15.25 Hz), −123.76 (d, br, 3F, F-3, $^4J_{F_1-F_3}$=15.25 Hz), −145.95 (dt, 3F, F-8, $^4J_{F_8-F_1}$=76.23 Hz, $^3J_{F_8-F_7}$=16.80 Hz), −149.89 (dt, 3F. F-5, $^4J_{F_5-F_4}$=54.77 Hz, $^3J_{F_5-F_6}$=16.80 Hz), −155.34 (dt, 3F, F-4, $^4J_{F_4-F_5}$=54.77 Hz, $^3J_{F_4-F_3}$=19.76 Hz), −160.96 (t, br, 3F, F-6, $^3J_{F_6-F_7}$=18.35 Hz), −161.87 (t, br, 3F, F-7, $^3J_{F_7-F_8}$=18.35 Hz).

Synthesis of Bis(cyclopentadienyl)zirconium Methyl Tris(β-perfluoronaphthyl)methylborate [(C$_5$H$_5$)$_2$ZrCH$_3$]$^+$[CH$_3$(C$_{10}$F$_7$)$_3$B]$^-$-(C)

Bis(cyclopentadienyl)zirconium dimethyl (3.8 mg, 0.015 mmol) and tris(β-perfluoronaphthyl)borane (11.6 mg, 0.015 mmol) were dissolved in the C$_6$D$_6$ in a J-Young NMR tube. The reaction occurred immediately to give bis (cyclopentadienyl)zirconium methyl tris(β-perfluoronaphthyl)methylborate and a byproduct, a μ-F bridged dimeric cationic species {[(C$_5$H$_5$)$_2$ZrMe]$_2$(μ-F)}$^{+[CH_3}$(C$_{10}$F$_7$)$_3$B]$^-$ in a ratio of 5:1. bis(cyclopentadienyl)zirconium Methyl Tris(β-perfluoronaphthyl)methylborate Analysis:

$^1$H NMR (C$_6$D$_6$, 23° C., 299.910 MHz): δ 5.57 (s, 10H, C$_5$H$_5$), 0.57 (s, br, 3H, B—CH$_3$), 0.43 (s, 3H, Zr—CH$_3$).

$^{19}$F NMR (C$_6$D$_6$, 23° C., 282.330 MHz): δ −110.71 (dd, 3F, F-1, $^4J_{F_1-F_8}$=73.12 Hz), −127.59 (d, br, 3F, F-3), −146.30 (dt, 3F, F-8, $^4J_{F_8-F_1}$=76.23 Hz), −147.55 (dt, 3F, F-5, $^4J_{F_5-F_4}$=55.05 Hz), −152.46 (dt, 3F, F-4, $^4J_{F_4-F_5}$=55.05 Hz), −156.90 (t, br, 3F, F-6), −158.33 (t, br, 3F, F-7).

{[(C$_5$H$_5$)$_2$ZrMe]$_2$(μ-F)}$^+$[CH$_3$(C$_{10}$F$_7$)$_3$B]$^-$ Analysis:

$^1$H NMR (C$_6$D$_6$, 23° C., 299.910 MHz): δ 5.60 (s, 20H, C$_5$H$_5$), 1.56 (s, br, 3H, B—CH$_3$), 0.26 (s, 6H, Zr—CH$_3$, $^3J_{H-F}$=2.4 Hz).

$^{19}$F NMR (C$_6$D$_6$, 23° C., 282.330 MHz): δ −88.32 (s, 1F, Zr—F—Zr), −108.58 (dd, 3F, F-1, $^4J_{F_1-F_8}$=73.41 Hz),

−124.24 (d, br, 3F, F-3), −146.03 (dt, 3F, F-8, $^4J_{F_8-F_1}$=76.23 Hz), −149.79 (dt, 3F, F-5, $^4J_{F_5-F_4}$=55.05 Hz), −155.23 (dt, 3F, F-4, $^4J_{F_4-F_5}$=54.77 Hz), −160.50 (t, br 3F, F-6), −161.45 (t, br, 3F, F-7).

Synthesis of (μ-Me) dimer salt: {[(C$_5$H$_5$)$_2$ZrMe]$_2$ (μ-Me)}$^+$[CH$_3$(C$_{10}$F$_7$)$_3$B]$^-$-(D)

Cp$_2$ZrMe$_2$ (7.5 mg, 0.030 mmol) and tris(β-perfluoronaphthyl)lborane (11.6 mg, 0.015 mmol) were dissolved in the C$_6$D$_6$ in a J-Young NMR tube. The reaction occurred immediately to give {[(C$_5$H$_5$)$_2$ZrMe]$_2$(μ-Me)}$^+$ [CH$_3$(C$_{10}$F$_7$)$_3$B]$^-$ and the byproduct, a μ-F bridged dimeric cationic species {[(C$_5$H$_5$)$_2$ZrMe]$_2$(μ-F)}$^{+[CH}$$_3$(C$_{10}$F$_7$)$_3$B]$^-$ in a ratio of 5:1.

{[(C$_5$H$_5$)$_2$ZrMe]$_2$(μ-Me)}$^+$[CH$_3$(C$_{10}$F$_7$)$_3$B]$^-$ analysis:

$^1$H NMR (C$_6$D$_6$, 23° C., 299.910 MHz): δ 5.65 (s, 20H, C$_5$H$_5$), 1.56 (s, br, 3H, B—CH$_3$), −0.07 (s, 6H, Zr—CH$_3$), −1.15 (s, 3H, Zr—CH$_3$—Zr).

$^{19}$F NMR (C$_6$D$_6$, 23° C., 282.330 MHz): δ −108.58 (dd, 1F, F-1, $^4J_{F_1-F_8}$=73.41 Hz), −124.24 (d, br, 1F, F-3), −146.03 (dt, 1F, F-8, $^4J_{F_8-F_1}$=76.23 Hz), −149.79 (dt, 1F, F-5, $^4J_{F_5-F_4}$=55.05 Hz), −155.23 (dt, 1F, F-4, $^4J_{F_4-F_5}$=54.77Hz), −160.50 (t, br, 1F, F-6), −161.45 (t, br, 1F, F-7).

Synthesis of (T-Butylamido)dimethyl (tetramethylcyclopentadienyl)silane-titanium Methyl Tris(β-perfluoronaphthyl)methylborate [(C$_5$(CH$_3$)$_4$) Si(CH$_3$)$_2$N(C(CH$_3$)$_3$)TiCH$_3$]$^+$[CH$_3$(C$_{10}$F$_7$)$_3$B]$^-$-(E)

(t-Butylamido)dimethyl(tetramethylcyclopentadienyl) silanetitanium dimethyl (4.9 mg, 0.015 mmol) and tris(β-perfluoronaphthyl)borane (11.6 mg, 0.015 mmol) were dissolved in the C$_6$D$_6$ in a J-Young NMR tube. The reaction occurred immediately to give the desired product. No μ-F bridged dimeric cationic species formed.

[(C$_5$(CH$_3$)$_4$)Si(CH$_3$)$_2$N(C(CH$_3$)$_3$)TiCH$_3$]$^+$[CH$_3$(C$_{10}$F$_7$)$_3$B]$^-$ analysis $^1$H NMR (C$_6$D$_6$, 23° C., 299.910 MHz): δ 1.847 (s, 3H, C$_5$Me$_4$), 1.658 (s, 3H, C$_5$Me$_4$), 1.610 (d, 3H, C$_5$Me$_4$, J$_{H-F}$=3 Hz), 1.466 (s, 3H, C$_5$Me$_4$), 1.085 (s, 9H, NCMe$_3$), 1.60 (br, 6H, Ti—Me, B—Me), 0.336 (s, 3H, SiMe$_2$), 0.179 (s, 3H, SiMe$_2$).

$^{13}$C NMR (C$_6$D$_6$, 23° C., 75.462 MHz): δ 141.21 (C$_5$Me$_4$), 139.17 (d, C$_5$Me$_4$, J$_{C-F}$=2.4 Hz), 138.68 (C$_5$Me$_4$), 136.21 (C$_5$Me$_4$), 105.54 (C$_5$Me$_4$), 66.67 (Ti—CH$_3$), 63.40 (NCMe$_3$), 33.03 (NCMe$_3$), 16.07 (C$_5$Me$_4$), 13.91 (C$_5$Me$_4$), 12.04 (C$_5$Me$_4$), 11.58 (C$_5$Me$_4$), 11.58 (C$_5$Me$_4$), 5.13 (SiMe$_2$), 4.54 (SiMe$_2$).

$^{19}$F NMR (C$_6$D$_6$, 23° C., 282.330 MHz): δ −110.42 (d, br, 3F, F-1, $^4J_{F_1-F_8}$=76 Hz), −127.13 (br, 3F, F-3), −145.94 (multi, 3F, F-8), −148.77 (multi, 3F, F-5), −152.63 (multi, 3F, F-4), −157.14 (t, 3F, F-6, $^3J_{F_6F_7}$=18 Hz), −158.58 (t, 3F, F-7, $^3J_{F_7F_8}$=18 Hz).

Synthesis of (μ-Me) dimer salt: [(C$_5$(CH$_3$)$_4$) Si(CH$_3$)$_2$N(C(CH$_3$)$_3$)TiCH$_3$ (μ-Me)]$^+$[CH$_3$(C$_{10}$F$_7$)$_3$B]$^-$-(F)

(t-Butylamido)dimethyl(tetramethylcyclopentadienyl) silanetitanium dimethyl (9.8 mg, 0.030 mmol) and tris(β-perfluoronaphthyl)borane (11.6 mg, 0.015 mmol) were dissolved in the C$_6$D$_6$ in a J-Young NMR tube. The reaction occurred immediately to give the desired product. No μ-F bridged dimeric cationic species formed.

[(C$_5$(CH$_3$)$_4$)Si(CH$_3$)$_2$N(C(CH$_3$)$_3$)$_{TiCH3}$(μ-Me)]$^+$[CH$_3$(C$_{10}$F$_7$)$_3$B]$^-$ analysis:

$^1$H NMR (C$_6$D$_6$, 23° C., 299.910 MHz): δ 1.898 (s, 6H, C$_5$Me$_4$), 1.574 (s, 6H, C$_5$Me$_4$), 1.547 (s, 6H, C$_5$Me$_4$), 1.524 (s, 6H, C$_5$Me$_4$), 1.114 (s, 9H, NCMe$_3$), 0.458 (s, 6H, Ti—Me), 0.364 (br, 3H, B—Me), 0.337 (s, 6H, SiMe$_2$), 0.284 (s, 6H, SiMe$_2$), −0.828 (s, 3H, Ti—Me—Ti).

$^{13}$C NMR (C$_6$D$_6$, 23° C., 75.462 MHz): δ 142.33 (C$_5$Me$_4$), 137.24 (C$_5$Me$_4$), 135.81 (C$_5$Me$_4$), 134.34 (C$_5$Me$_4$), 102.41 (C$_5$Me$_4$), 64.82 (Ti$_{13}$ $_{CH3}$), 61.59 (NCMe$_3$), (Ti—CH$_3$—Ti), 33.70 (NCMe$_3$), 15.67 (C$_5$Me$_4$), 14.57 (C$_5$Me$_4$), 11.90 (C$_5$Me$_4$), 11.65 (C$_5$Me$_4$), 5.44 (SiMe$_2$), 4.26 (SiMe$_2$).

$^{19}$F NMR (C$_6$D$_6$, 23° C., 282.330 MHz): δ −108.29 (dd, 3F, F-1, $^4J_{F_1-F_8}$=76 Hz, $^3J_{F_1-F_3}$=16 Hz), −123.18 (br, 3F, F-3), −145.94 (dt, 3F, F-8, $^4J_{F_8-F_1}$=73 Hz, $^3J_{F_8-F_7}$=18 Hz), −149.99 (dt, 3F, F-5, $^4J_{F_5-F_4}$=55 Hz, $^3J_{F_5-F_7}$=17 Hz), −155.41 (dt, 3F, F-4, $^4J_{F_4F_5}$=55 Hz, $^3J_{F_4-F_3}$=18 Hz, −161.32 (t, 3F, F-6 $^3J_{F_6F_7}$=18 Hz), −162.19 (t, 3F, F-7, $^3J_{F_7-F_8}$=18 Hz).

Synthesis of (T-Butylamido)dimethyl (tetramethylcyclopentadienyl)silanezirconium Methyl Tris(β-perfluoronaphthyl)methylborate [(C$_5$(CH$_3$)$_4$)Si(CH$_3$)$_2$N(C(CH$_3$)$_3$)ZrCH$_3$]$^+$[CH$_3$(C$_{10}$F$_7$)$_3$B]$^-$-(G)

(t-Butylamido)dimethyl(tetramethylcyclopentadienyl) silanezirconium dimethyl (5.6 mg, 0.015 mmol) and tris(β-perfluoronaphthyl)borane (11.6 mg, 0.015 mmol) were dissolved in the C$_6$D$_6$ in a J-Young NMR tube. The reaction occurred immediately to give the desired product. No μ-bridged dimeric cationic species formed.

[(C$_5$(CH$_3$)$_4$)Si(CH$_3$)$_2$N(C(CH$_3$)$_3$)ZrCH$_3$]$^+$[CH$_3$(C$_{10}$F$_7$)$_3$B]$^-$ analysis:

$^1$H NMR (C$_6$D$_6$, 23° C., 299.910 MHz): δ 1.81 (s, 3H, C$_5$Me$_4$), 1.77 (s, 3H, C$_5$Me$_4$), 1.64 (s, 3H, C$_5$Me$_4$), 1.58 (s, 3H, C$_5$Me$_4$), 1.43 (s, br, B—CH$_3$), 1.13 (s, 9H, NCMe$_3$), 0.47 (s, 3H, Zr—Me), 0.28 (s, SiMe$_2$), 0.19 (S, SiMe$_2$).

$^{19}$F NMR (C$_6$D$_6$, 23° C., 282.330 MHz): δ −111.05 (br, 3F, F-1), −127.36 (br, 3F, F-3) −146.01 (dt, 3F, F-8, $^4J_{F_8-F_1}$=76 Hz, $^3J_{F_8-F_7}$=17 Hz), −147.82 (br, 3F, F-5), −152.51 (br, 3F, F-4), −157.26 (br, 3F, F-6), −158.64 (br, 3F, F-7).

Polymerization Tests

Ethylene was polymerized in a 250-mL round-bottom flask attached to a high-vacuum line at 25° C. Catalysts (0.15 mmol) were generated by mixing in toluene (2 mL) in a dry box the metal complex and tris(β-perfluoronaphthyl)borane. The solution was quickly injected using a gas-tight syringe equipped with a spraying needle into a rapidly stirred flask containing 100 mL of toluene which was pre-saturated under 1 atm of purified ethylene. The polymerization was quenched with acidic CH$_3$OH after a short time period. Comparative runs using trispentafluorophenylborane cocatalyst were conducted under substantially the same polymerization conditions. The polyethylene product was collected by filtration, washed with methanol, and dried under high vacuum to a constant weight. Results are contained in Table 1.

TABLE 1

| Run | Complex | Rxn. Time (min.) | Yield (g) | activity (g/mole.atm.hr) | Mw (×10$^5$) | Mw/Mn[1] |
|---|---|---|---|---|---|---|
| 1 | A | 0.5 | 1.20 | 9.6 × 10$^6$ | 0.87 | 1.88 |
| 2 | B | 0.5 | 0.89 | 7.1 × 10$^6$ | 0.76 | 1.61 |
| 3 | C | 1.1 | 0.87 | 3.2 × 10$^6$ | 0.97 | 1.67 |
| 4 | D | 1.1 | 0.79 | 2.9 × 10$^6$ | 0.96 | 1.54 |
| 5 | E | 30 | 2.50 | 3.3 × 10$^5$ | 13.3 | 3.20 |
| 6 | * | 10 | 0.21 | 8.4 × 10$^4$ | 10.6 | 9.54 |

TABLE 1-continued

| Run | Complex | Rxn. Time (min.) | Yield (g) | activity (g/ mole.atm.hr) | Mw (×10$^5$) | Mw/Mn[1] |
|---|---|---|---|---|---|---|
| 7 | G | 70 | 0.08 | 3.8 × 10$^3$ | 14.8 | 2.47 |
| 8 | ** | 20 | 0 | — | — | — |

[1]GPC relative to polystyrene standard
*comparative, catalyst = (t-butylamido) dimethyl (tetramethylcyclopentadienyl)silanetitanium methyl tris(pentafluorophenyl) methylborate
**comparative, catalyst = (t-butylamido) dimethyl (tetramethylcyclopentadienyl)silanezirconium methyl tris (pentafluorophenyl)methylborate

What is claimed is:

1. A compound corresponding to the formula: $L^+B^-(C_6F_5)_3(C_{10}F_7)$, $L^+B^-(C_6F_5)_2(C_{10}F_7)_2$, $L^+B^-(C_6F_5)_1(C_{10}F_7)_3$, or $L^+B^-(C_{10}F_7)_4$, where $L^+$ is a cation of a Bronsted acid, ferrocenium, a carbonium cation, a silylium cation, $Ag^+$ or the cationic derivative of a Group 3–10 metal complex catalyst.

2. A compound according to claim 1, wherein $L^+$ is an ammonium cation of the formula $HN^+R_3$, wherein R is $C_{1-50}$ hydrocarbyl.

* * * * *